Figure 1A:
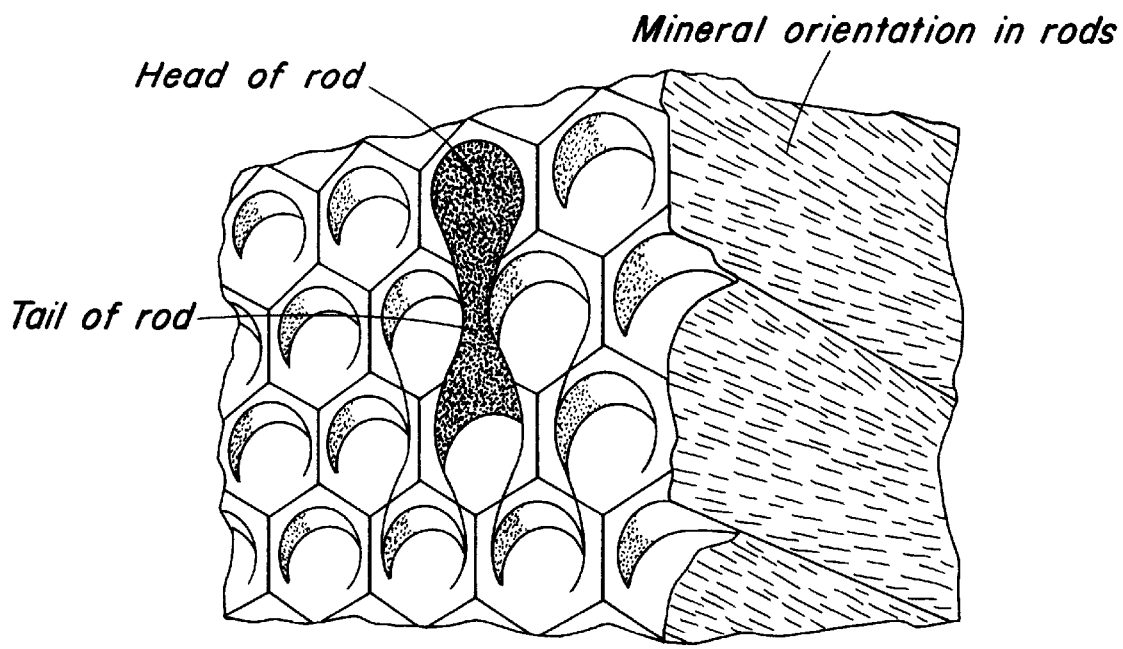

United States Patent

Lindskog et al.

[11] Patent Number: 6,027,341
[45] Date of Patent: Feb. 22, 2000

[54] DENTAL CAVITY CONDITIONING

[75] Inventors: Sven Lindskog, Stockholm; Leif Blomlöf, Lidingö, both of Sweden

[73] Assignee: Peridoc AB, Stockholm, Sweden

[21] Appl. No.: 08/793,866

[22] PCT Filed: Sep. 14, 1995

[86] PCT No.: PCT/SE95/01040

§ 371 Date: Mar. 11, 1997

§ 102(e) Date: Mar. 11, 1997

[87] PCT Pub. No.: WO96/09028

PCT Pub. Date: Mar. 28, 1996

[30]     Foreign Application Priority Data

Sep. 22, 1994 [SE] Sweden .................................. 9403192

[51] Int. Cl.$^7$ ...................................................... A61C 5/00
[52] U.S. Cl. ...................... 433/215; 433/226; 433/228.1; 106/35
[58] Field of Search ..................... 433/215, 226, 433/228.1; 106/35

[56]              References Cited

U.S. PATENT DOCUMENTS

| | | |
|---|---|---|
| 4,758,163 | 7/1988 | Goldman .................................. 433/229 |
| 4,802,950 | 2/1989 | Croll ........................................ 156/629 |
| 4,850,872 | 7/1989 | Goldman et al. ........................ 433/215 |
| 5,348,476 | 9/1994 | Cohen et al. ............................ 433/220 |
| 5,401,783 | 3/1995 | Bowen .................................. 433/228.1 |

OTHER PUBLICATIONS

"A Scanning Electron Microscopic Observation of Inner Carious Dentin After Cleansing and of the Dentin–Resin Interface", Zhizhong Cao et al., *Quintessence International*, vol. 23, No. 6, 1992, pp. 439–444.

"Smear Removal Agents: A Quantitative Study in Vivo and in Vitro", S.D. Meryon et al., *Journal of Prosthetic Dentistry*, vol. 57, No. 2, Feb. 1987, pp. 174–179.

*Primary Examiner*—John J. Wilson
*Attorney, Agent, or Firm*—Burns, Doane, Swecker & Mathis, L.L.P.

[57]              ABSTRACT

A process for the conditioning of dental cavities by etching in preparation for bonding restorations to enamel and dentin, comprising the steps: a) etching the dentin part of a dental cavity using an aqueous composition containing, as an active constituent, EDTA in an effective amount, and b) etching the enamel part of said cavity using a conventional etching acid; and a kit for use in such process for conditioning.

17 Claims, 2 Drawing Sheets

Head of rod
Tail of rod
Mineral orientation in rods

Head  Tail
Enamel rod
Rod sheath
Rod core

DENTAL CAVITY CONDITIONING

The present invention relates to a process for the conditioning of dental cavities by etching in preparation for bonding restorations to enamel and dentin, and the invention also covers a kit for use in such conditioning process.

BACKGROUND OF THE INVENTION

Enamel is the hardest biologic tissue found in the body and it forms a protective layer covering the crowns of teeth. It is composed of interlocking rods which, to more than 96%, are constituted by hydroxyapatite. The rods are deposited in keyhole shapes each of which comprise a head and a tail surrounded by a sheath (cf. FIG. 1 as enclosed). Enamelin, a protein unique to enamel, can be found in minute amounts surrounding individual hydroxyapatite crystallites predominantly in the sheath (for a review see Avery J K. Essentials of Oral Histology and Embryology. A Clinical Approach. St. Louis, Mosby, 1992).

The body of the tooth, both the crown and the root thereof, is constituted by dentin. Dentin is composed of an organic matrix of collagen fibers (on average 20% by weight), in which hydroxyapatite crystallites (on average 70% by weight) are dispersed. The remaining 10% of the dentin is constituted by water. Dentin tubules, approximately 1 $\mu$m in diameter and of a density amounting to 30 000 to 50 000 tubules per mm2, run from the centrally located pulp to the periphery of the body of dentin (cf. FIG. 2 as enclosed). The walls of the tubules are made up of peritubular dentin which is approximately 40% more highly mineralized than the intertubular dentin in between the tubules. The water component of dentin is mainly found in the dentin tubules (for a review, see Avery 1992, above).

The bonding of dental restorations to dental mineralized tissues is the last step in filling therapy (for details, see Heymann, H., Bayne, S. Current Concepts in dentin bonding. Journal of the American Dental Association 1993, 124, 27–35). The process starts with mechanical removal of carious enamel and dentin followed by cavity preparation. The cavity walls are subsequently pretreated before insertion of the filling material in order to increase adherence of the material to the walls and to minimize gap formation. This process is generally referred to as bonding and relies on two principles:

Mechanical interlocking of the resin-based restoration to irregularities in the mineralized surface.

Chemical bonding of the resin-based restoration to exposed collagen.

The bonding usually involves an initial step of surface etching using ortho-phosphoric acid, such etching having for its purpose to:

remove any debris, such as smear and bacteria, resulting from the mechanical cavity preparation;

maximize the surface area of the enamel cavity walls by eroding the more heavily mineralized enamel rod heads. This produces protruding ridges of rod sheaths for mechanical interlocking with resin-based restorations;

expose collagen in the dentin surface to make the fibers accessible for chemical bonding to resin-based restorations.

Etching is, by definition, the selective removal of parts or components from a solid surface through the action of an etching agent, such as solutions of acids or other substances. Etching does not, however, implicate erosion of the surface to remove a complete surface layer. The purpose of the etching of exposed dental mineralized tissues after cavity preparation is not the same for all tissues involved. Thus, in regard to a dentin surface the purpose is to selectively remove smear and hydroxyapatite leaving an exposed layer of collagen. With regard to an enamel surface the purpose is to increase the surface area. available for bonding by removing hydroxyapatite from the more highly mineralized enamel rods.

SUMMARY OF THE INVENTION

The principle object of the present invention is to provide a process for the conditioning of dental cavities by etching considering the different tissues involved in such etching.

Another object of the invention is to selectively remove smear and hydroxyapatite from a dentin surface so as to form an exposed layer of collagen.

A further object of the invention is to increase the surface area available for bonding to an enamel surface, such increase residing in the removal of hydroxyapatite from the more highly mineralized enamel rods.

Yet another purpose of the invention is to provide a kit for use in such conditioning of dental cavities by etching.

For these and other objects that will be clear from the following disclosure the invention provides for a process for the conditioning of dental cavities by etching in preparation for bonding restorations to enamel and dentin, said process comprising the following steps:

a) etching the dentin part of a dental cavity using an aqueous composition containing, as an active constituent, EDTA in an effective amount, and b) etching the enamel part of said cavity using a conventional etching acid.

Although any conventional etching acid can be used in step b) of the process it is preferred to use an acid selected from phosphoric and citric acids. The etching under step b) above is performed for a fairly short period of time, such as less than about 25 seconds.

With regard to the etching agents used in steps a) and b) above the EDTA-containing agent is suitably in the form of an aqueous solution having a pH of about neutral. The etching acid used in step b) has suitably a pH of about 1 and is also suitably constituted by an aqueous solution, such as a saturated citric acid solution or a phosphoric acid solution having a concentration of about 37%.

The invention also provides for a kit for use in such conditioning of dental cavities by etching in preparation for bonding restorations to enamel and dentin, said kit comprising the following items:

a) a first container holding an aqueous composition containing EDTA;

b) a second container holding an aqueous composition containing a conventional etching acid; and c) instructions for the use of the kit.

A preferred embodiment of such kit contains as a composition of the first container (based on the water contents of the composition):

EDTA in an amount of about 22 to 27% by weight;

sodium hydroxide as a pH-controlling agent in an amount resulting in a pH within the range about 6.5 to about 7.5; and a viscosity-increasing agent constituted by carboxymethyl cellulose (CMC) or a salt thereof in an amount of from about 1% by weight to about 5% by weight.

A particularly preferred embodiment of such kit is one wherein:

the amount of EDTA is about 25% by weight;

the pH of the composition is around neutral pH7; and the viscosity-increasing agent is sodium carboxymethyl cellulose in an amount of about 3 to 5% by weight.

As explained above the etching of the dentin part of a dental cavity is performed by using ethylene-diaminotetraacetic acid (EDTA), said substance being present in an aqueous environment in combination with an aqueous matrix. EDTA is an agent which chelates divalent cations, such as $Ca^{2+}$, $Mg^{2+}$, $Fe^{2+}$ and $Pb^{2+}$. It has found use in infusion solutions for detoxification and as an anticoagulant in vivo. In vitro it has found a variety of uses, such as to detach cells from solid substrata (Paul J. Cell and Tissue Culture. London: Churchill, 1975; Adams R L P. Cell Culture for Biochemists, Amsterdam: Elsevier, 1980), decalcify tissue specimens before sectioning and staining (Brain, EB. The Preparation of Decalcified Sections. Springfield: Charles C Tomas Publisher, 1966; Dickson G R. Methods of Calcified Tissue Preparation. Amsterdam: Elsevier, 1984) and as a detergent in biochemical analysis.

By the use of conventional etching agents operating at about pH 1, such as phosphoric or citric acid, not only the mineral component of exposed dentin surfaces is dissolved but also the collagenous matrix. Accordingly, collagen is dissolved at acid pH's by acids, such as citric acid, already at low concentrations (Trelstad RT. Native collagen fractionation. In: Immunochemistry of the Extra-cellular Matrix. Volume 1. Methods. Ed: Furthmayr H. Boca Raton: CRC Press, 1982: 31–41). It is true that EDTA can also dissolve parts of collagen molecules or superstructures, but this effect is negligible during the short exposure required in the conditioning of dental cavities. Thus, EDTA etching in contrast to conventional etching agents, will selectively remove hydroxyapatite but not the collagenous matrix of dentin.

As a conventional etching acid used in step b) of the process of the invention phosphoric and citric acids are preferred. Particularly preferred is ortho-phosphoric acid ($H_3PO_4$) which is a moderately strong organic acid ($pK_a$= 2.15), which in aqueous solution can form insoluble complexes with calcium. For decalcification of mineralized tissues in accordance with the present invention it is preferred to use an about 10–37% by weight aqueous solution having a pH around 1.

To facilitate introduction of the EDTA into the composition matrix it is preferred to include a pH-controlling agent in an amount resulting in a pH of the aqueous phase of the composition lying within the range from about 6 to about 8. A particularly preferred range is from about 6.5 to about 7.5, i.e. around neutral, pH 7.

Said pH-controlling agent can be any alkaline compound or substance compatible with the intended use of the composition, and the agent may also be constituted by a suitable buffer. Among alkaline compounds there may be mentioned ammonia and hydroxides of alkali metals and alkaline earth metals. Particularly preferred alkaline compounds are sodium hydroxide, potassium hydroxide and calcium hydroxide.

As indicated above the etching agents or composition used in the process of the present invention are of an aqueous nature and may be constituted by an aqueous composition. For ease of application of each composition it is preferred that it is in the form of a viscous aqueous solution, increased viscosity being provided by a viscosity-increasing agent. Such agent may be constituted by a polysaccharide and may be selected from celluloses and derivatives thereof, starches and derivatives thereof, plant gums, capsular microbial polysaccharides and algal polysaccharides.

Among preferred polysaccharides there may be mentioned celluloses and derivatives thereof, e.g. ethyl celluloses, hydroxyethyl celluloses, carboxymethyl celluloses and salts thereof, and starches and starch derivatives, such as hydroxyethyl starch. A particularly preferred viscosity increasing agent is sodium carboxymethyl cellulose.

Among microbial polysaccharides there may be xanthan gum, curdlan, pullulan, dextran, and among algal polysaccharides there may be mentioned agar, carageenans, alginic acid.

The concentration of the polysaccharide used in the compositions used in accordance with the invention may vary within broad limits but a practical upper limit is about 25% by weight of the polysaccharide based on the weight of the composition. However, much lower percentages may be used and a concentration of the order of up to 10% by weight of the polysaccharide, such as about 1 to about 5% by weight, are practically conceivable.

As an alternative to using a polysaccharide as a viscosity-increasing agent there may be used agents selected from proteins and glycoproteins, such as gelatin, denatured structural proteins and proteoglycans.

It is preferred that the compositions contain water as a major component, and their contents of the etching ingredient, EDTA or conventional acid, respectively, may be a concentration near saturation or at saturation, such as about 27% by weight of EDTA based on the water contents of the composition. At around neutral pH the saturation point for EDTA lies between about 22 and 27% by weight based on the water contents of the composition, such as about 25%.

The expression "near saturation" means in this disclosure a concentration which is no less than about 80% and especially no less than about 90% of the concentration at saturation.

To facilitate application of the compositions used according to the invention onto the cavity surface to be conditioned it is preferred that the composition has a relatively high viscosity, and the composition may for this purpose take the form of a gel or a semi-fluid material. Such state or form can be obtained by using a suitable polysaccharide in a relatively small amount, such as up to about 5% by weight based on the water contents of the composition, a preferred range being from about 2 to about 5% by weight.

In regard to the nature of the conventional etching acid used, phosphoric and citric acids are preferred, particularly ortho-phosphoric acid ($H_3PO_4$) in a concentration to result in a fairly low pH at around 1. The concentration of the phosphoric acid is not particularly critical, but may be up to about 40% by weight, a preferred lower limit being about 10% by weight. The range about 30 to about 40, such as about 37% by weight is particularly preferred.

Figure 1B:
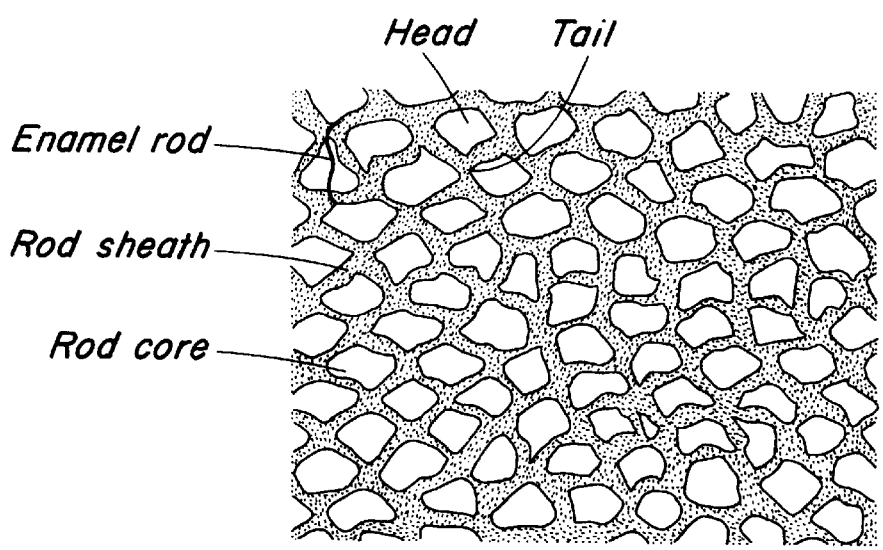
Figure 2:
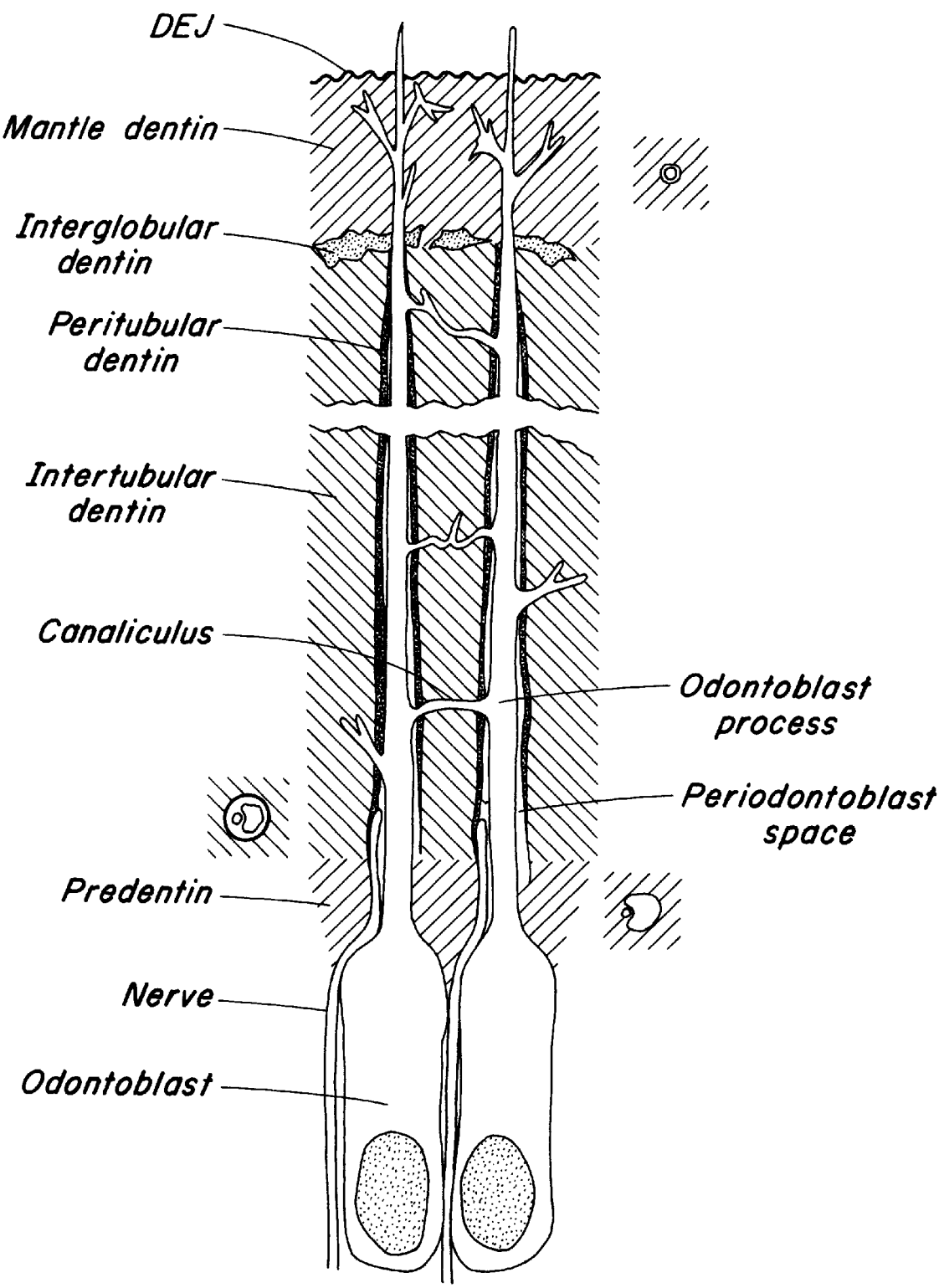

The present invention will be further illustrated below with reference to specific examples which, however, must not be construed to limit the scope of the invention otherwise than as defined in the appended claims. In these examples percentages refer to weight unless otherwise stated. To facilitate the understanding of the invention a drawing is appended, wherein:

FIG. 1 illustrates the structure and composition of enamel through a perspective view (i.e., FIG. 1A) and a plan view, (i.e., FIG. 1B) respectively, of a section of enamel tissue; and FIG. 2 illustrates a cross-section of a tooth clarifying the structure and composition of dentin.

EXAMPLE 1

Preparation of etching compositions

Aqueous solutions of citric acid at saturation, pH about 1, ortho-phosphoric acid, at a concentration of 37% by weight, pH about 1, and EDTA at a concentration of 25%, pH about 7, are prepared for use in the experiments.

EXAMPLE 2
Preparation of an EDTA-composition

An aqueous composition is prepared by dissolving about 25% of EDTA in water using NaOH as a pH-controlling agent to give a pH about 7. To the resulting solution sodiumcarboxymethylcellulose is added to form a gel-like viscous composition which is easy to handle in the conditioning procedure and does not flow away from the area to be treated. For obtaining a suitable viscosity a quantity of sodiumcarboxymethylcellulose within the range about 3 to about 5% is suitable.

EXAMPLE 3
Preparation of a conventional etching composition

An aqueous solution of ortho-phosphoric acid having an acid concentration of about 37% is prepared resulting in a pH of the solution of about 1. The resulting solution is made viscous in the same manner as described in Example 2 above.

EXAMPLE 4

Extracted human teeth having dental cavities with exposed dentin and enamel are immersed into the aqueous solutions prepared according to Example 1 above. The teeth are held in the solutions for more than 10 min and are then prepared for examination.

All the solutions remove smear and debris within a short period of time (less than 1 min). Conventional acid etching using citric or phosphoric acid produce an essentially smooth dentin surface with only occasional morphous deposits in the area between the dentinal tubules, but no fibers are visible. Dentinal tubules are clearly visible and appear widened. Etching using EDTA produces a completely different texture with the dentin in-between dentinal tubules consistently displaying a fibrous mesh-work with individual fibers clearly visible and comparable in size to collagenous fibers. Conventional acid etching erodes enamel rods already after 5 to 20 seconds uncovering protruding rod sheaths. EDTA produces similar result only upon exposure for more than 10 min.

The results from the experiments performed show that the collagenous matrix is left intact following EDTA etching, while etching with conventional etching agents, such as citric or phosphoric acid, will dissolve both the mineral and the collagenous matrix of dentin. Etching using EDTA of cavities in preparation for bonding of resin-based fillings are therefore preferred over etching using citric or phosphoric acid. Etching of enamel with EDTA is, however, clinically impractical due to the need for exposure times in excess of 10 min. Therefore, enamel is preferably etched with a conventional etching acid, such as citric or phosphoric acid, the etching taking less than 20 seconds for obtaining the desired result. Thus, the invention is based on the concept of using different etching compositions for selective use on dentin and enamel, the compositions being based on EDTA and a conventional etching acid, respectively. For practical purposes the etching compositions are preferably in a viscous form to allow full control of application and to avoid accidental etching of dentin with conventional etching acid, such as phosphoric acid. It is to be noted that etching the dentin part of the dental cavity using EDTA need not be restricted to the dentin part only, since the EDTA composition does not deleteriously affect the enamel part of the cavity. However, care should be taken that the conventional etching acid composition is excluded from coming into contact with the dentin part of the dental cavity.

We claim:

1. A process for the conditioning of dental cavities by etching in preparation for bonding restorations to enamel and dentin, comprising the steps:
    a) etching the dentin part of a dental cavity using an aqueous composition containing, as an active constituent, EDTA in a concentration which is no less than about 90% of the concentration at saturation of said acid;
    b) etching the enamel part of said cavity using an acid selected from the group consisting of phosphoric acid and citric acid.

2. A process according to claim 1, wherein the etching under step b) is performed for a period of less than about 25 seconds.

3. A process according to claim 1, wherein the etching acid used in step b) has a pH of about 1.

4. A process according to claim 3, wherein the etching acid used is constituted by an aqueous saturated citric acid solution.

5. A process according to claim 3, wherein the etching acid used is constituted by an aqueous solution of ortho-phosphoric acid having a concentration of about 37%.

6. A process according to claim 1, wherein the etching in step a) is performed using an aqueous composition of EDTA comprising a pH-controlling agent in an amount resulting in a pH of the composition lying within the range from about 6 to about 8.

7. A process according to claim 6, wherein said pH lies within the range from about 6.5 to about 7.5.

8. A process according to claim 7, wherein said pH-controlling agent is selected from the group consisting of alkaline compounds and buffers.

9. A process according to claim 7, wherein said aqueous composition of step a) is in the form of a viscous solution that does not flow away from the area to be treated.

10. A process according to claim 6, wherein said pH-controlling agent is selected from the group comprising alkaline compounds and buffers.

11. A process according to claim 10, wherein said agent is an alkaline compound selected from ammonia and hydroxides of alkali metals and alkaline earth metals.

12. A process according to claim 11, wherein said aqueous composition of step a) is in the form of a viscous solution that does not flow away from the area to be treated.

13. A process according to claim 10, wherein said aqueous composition of step a) is in the form of a viscous solution that does not flow away from the area to be treated.

14. A process according to claim 6 wherein said aqueous composition of step a) is in the form of a viscous solution that does not flow away from the area to be treated.

15. A process according to claim 14, wherein said aqueous composition of step a) comprises a viscosity-increasing agent selected from the group consisting of polysaccharides, proteins, and glycoproteins.

16. A process according to claim 15, wherein said viscosity-increasing agent is selected from the group consisting of celluloses and derivatives thereof, starches and derivatives thereof, plant gums, capsular microbial polysaccharides, and algal polysaccharides.

17. A process according to claim 16, characterized in that said viscosity-increasing agent is sodium carboxymethyl cellulose.

* * * * *